United States Patent [19]
Eriksen et al.

[11] Patent Number: 6,043,202
[45] Date of Patent: Mar. 28, 2000

[54] SHAMPOO COMPOSITIONS AND OIL COMPOSITIONS AND METHODS FOR TREATMENT OF CRADLE CAP

[76] Inventors: Karla S. Eriksen, 1917 Ellis St., San Francisco, Calif. 94115; Deborah Osburn, 855 Spring St., Sausalito, Calif. 94965

[21] Appl. No.: 09/036,540

[22] Filed: Mar. 6, 1998

[51] Int. Cl.⁷ .............................. A61K 7/045; C11D 3/38
[52] U.S. Cl. ........................ 510/119; 510/463; 514/880; 514/881
[58] Field of Search .................................... 510/119, 463; 514/880, 881

[56] References Cited

U.S. PATENT DOCUMENTS

| | | | |
|---|---|---|---|
| 4,835,148 | 5/1989 | Barford et al. | 514/179 |
| 4,893,955 | 1/1990 | Zielinski | 401/7 |
| 5,425,954 | 6/1995 | Thompson et al. | 424/401 |
| 5,470,574 | 11/1995 | Kosuge et al. | 424/401 |
| 5,817,089 | 10/1998 | Tankovich et al. | 606/9 |

*Primary Examiner*—Yogendra Gupta
*Assistant Examiner*—John M Petruncio
*Attorney, Agent, or Firm*—Peters Verny; Jones & Bikas, LLP

[57] ABSTRACT

The present invention concerns an improved shampoo composition, an improved oil composition and an improved method for the treatment of cradle cap (seborrhea dermatitis) primarily in infants and small children. In the improved method, the scalp of an infant is treated with the improved oil followed by gentle brushing and the scalp is then contacted with the improved shampoo and water. Usually the cradle cap condition is eliminated in 1 to 5 days. A kit including the oil, shampoo, sponge, brush, fine toothed comb and optional separate instructions are described.

20 Claims, 1 Drawing Sheet

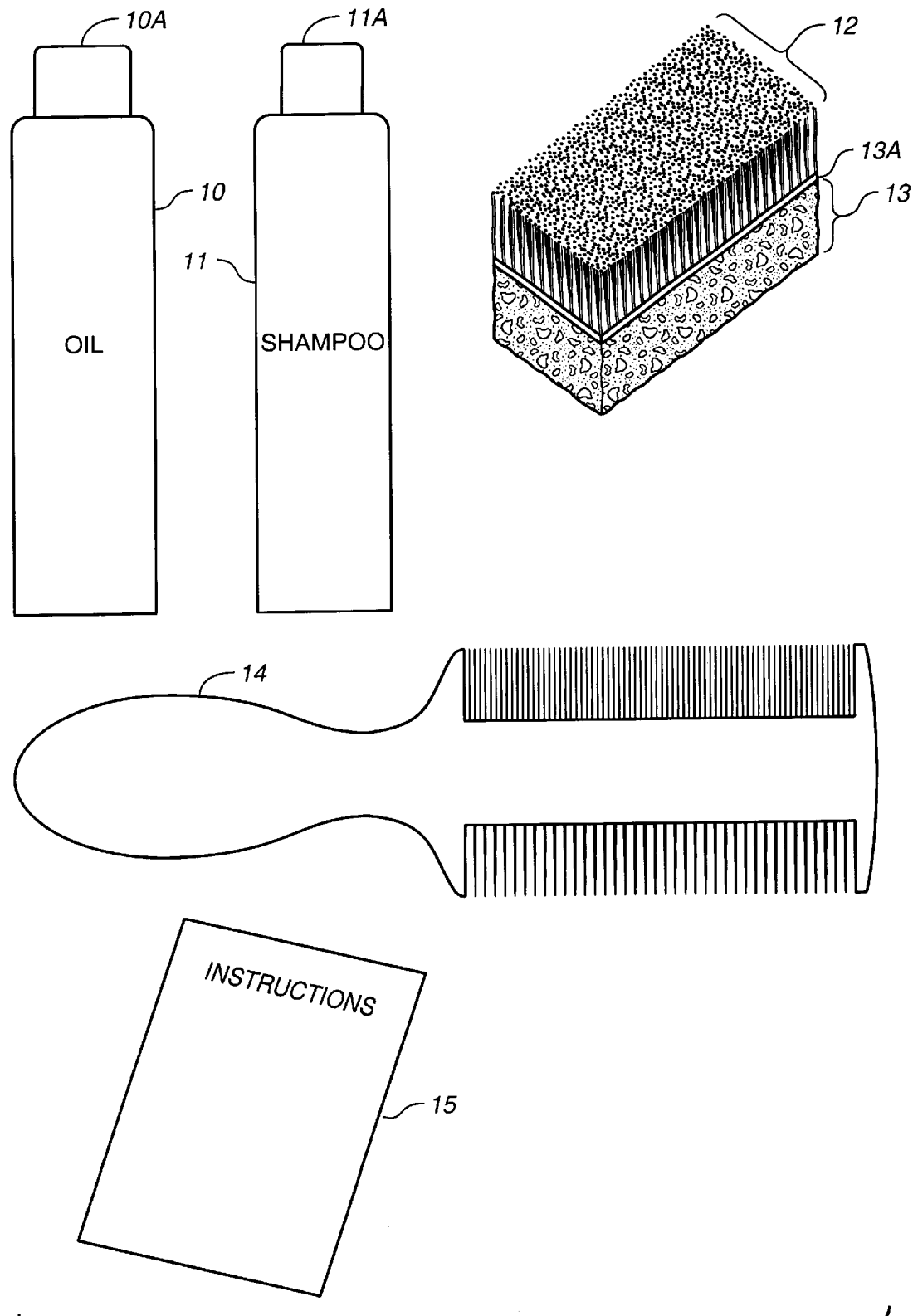
FIG._1

SHAMPOO COMPOSITIONS AND OIL COMPOSITIONS AND METHODS FOR TREATMENT OF CRADLE CAP

BACKGROUND OF THE INVENTION

1. Field of the Invention

The present invention concerns shampoo compositions and oil compositions and methods using these compositions for the treatment of cradle cap.

2. Description of Related Art

Cradle cap is usually a recurring condition most prevalent in infants between about one and nine months. Thick yellow scales occur in patches over the scalp and may also occur on the face, neck and behind the ears. Cradle cap is a form of seborrhea dermatitis. Although unsightly, cradle cap is usually harmless but can pose a threat to health if the scalp becomes infected.

There are a number of individual treatments described by various sources to alleviate the cradle cap conditions, including but not limited to:

Tea mixture

Oil/herb mixture

Olive oil

Vitamin E

Mild dandruff shampoo

Geranium/eucalyptus/almond oil

Camomile/chamomile

The difficulty of the existing treatments is that the use of the oils and/or shampoos, as individual ingredients are not effective, are not well quantified and are not used in combination with each other for rapid treatment of cradle cap.

In some cases cradle cap persists regardless of the existing treatments for months or for years.

From this description, it is apparent that a need exists for improved oils, improved shampoos and methods to provide rapid and effective treatment of cradle cap. The present invention provides a solution to this need by using an effective combination of oil components and allowing the oil to loosen the cradle cap scales, a fine-toothed comb to lift the cap, and a shampoo to wash out the scales.

SUMMARY OF THE INVENTION

The present invention concerns shampoo compositions and oil compositions and methods for treatment of cradle cap.

In particular, the present invention concerns a therapeutic shampoo compositions, primarily for infants, to reduce or eliminate the condition of cradle cap, which shampoo composition comprises:

the following components present in between about the range weight present indicated:

TABLE 1

Broad Shampoo Composition

| COMPONENTS | PRESENT IN WEIGHT PERCENT |
|---|---|
| purified soft water | 50 to 95 |
| PEG (80 sorbitan laurate) | 1 to 10 |
| PEG (150 distearate) | 0.1 to 1 |
| disodium - lauroamphodiacetate | 1 to 10 |
| sodium laureth (13 carboxylate) | 1 to 10 |
| cocoamidopropyl hydroxy-sultane | 1 to 10 |
| decyl glucoside | 1 to 10 |
| tea tree oil | 1 to 10 |
| evening primrose oil | 0.1 to 0.9 |
| aloe barbadensis | 0.1 to 0.9 |
| chamomile extract | 0.1 to 0.9 |
| disodium EDTA | 0.1 to 0.9 |
| citric acid | 0.1 to 0.9 |
| grapefruit seed extract | 0.1 to 0.9 |
| methylparaben | 0.1 to 0.9 |
| propylparaben | 0.01 to 0.09 |
| annatto extract | 0.01 to 0.09 |
| caramel | 0.01 to 0.09 |
| panthenol | 0.1 to 0.9 |
| vitamin E acetate | 0.1 to 0.9 |
| eucalyptus oil | 0.1 to 0.9 |

In another aspect, the present invention relates to therapeutic oil composition for infants to reduce or eliminate the disease condition of cradle cap, which oil composition comprises:

the following compounds which are present in between that weight percent range indicated:

TABLE 2

Broad Oil Composition

| safflower oil | 50 to 90 |
|---|---|
| sweet almond oil | 5 to 25 |
| tocopheryl acetate | 0.1 to 1 |
| beta - carotene | 0.001 to 0.01 |
| tea tree oil | 1 to 10 |
| propylparaben | 0.01 to 0.09 |
| eucalyptus oil | 0.1 to 1 |
| vitamin A | 0.01 to 0.1 |
| vitamin B | 0.01 to 0.1 |

In another aspect, the present invention relates to an improved method to treat cradle cap in a mammal, preferably a human being, which method comprises:

(a) contacting the scalp or related area of a human being in need of treatment with a therapeutic amount of an oil of the composition:

| COMPONENTS PRESENT IN | WEIGHT PERCENT |
|---|---|
| safflower oil | 50 to 90 |
| sweet almond oil | 5 to 25 |
| tocopheryl acetate | 0.1 to 1 |
| beta - carotene | 0.001 to 0.01 |
| tea tree oil | 1 to 10 |
| propylparaben | 0.01 to 0.09 |
| eucalyptus oil | 0.1 to 1 |
| vitamin A | 0.01 to 0.1, and |
| vitamin B | 0.01 to 0.1; | rubbing the therapeutic oil in thoroughly into the area exhibiting cradle cap and allowing the oil to remain on the skin surface for between about 1 and 60 min followed by using a brush to gently loosen the scales on the scalp and removing the scales;

(b) contacting the scalp or related area of the human being with an effective amount of the improved shampoo of the composition:

| COMPONENTS PRESENT IN | WEIGHT PERCENT |
| --- | --- |
| purified soft water | 50 to 95 |
| PEG (80 sorbitan laurate) | 1 to 10 |
| PEG (150 distearate) | 0.1 to 1 |
| disodium - lauroamphodiacetate | 1 to 10 |
| sodium laureth (13 carboxylate) | 1 to 10 |
| cocoamidopropyl hydroxysultane | 1 to 10 |
| decyl glucoside | 1 to 10 |
| tea tree oil | 1 to 10 |
| evening primrose oil | 0.1 to 0.9 |
| aloe barbadensis | 0.1 to 0.9 |
| chamomile extract | 0.1 to 0.9 |
| disodium EDTA | 0.1 to 0.9 |
| citric acid | 0.1 to 0.9 |
| grapefruit seed extract | 0.1 to 0.9 |
| methylparaben | 0.1 to 0.9 |
| propylparaben | 0.01 to 0.09 |
| annatto extract | 0.01 to 0.09 |
| caramel | 0.01 to 0.09 |
| panthenol | 0.1 to 0.9 |
| vitamin E acetate | 0.1 to 0.9, and |
| eucalyptus oil | 0.1 to 0.9; | and water to remove the oil and loose cradle cap particles;

(c) repeating step (a) and step (b) as needed for a 1 to 5 day period or until the cradle cap condition disappears. If the condition persists, or if inflammation is present, a physician should be contacted immediately.

The present invention also includes the kit of articles shown in FIG. 1.

BRIEF DESCRIPTION OF THE FIGURE

FIG. 1 is a representation of the components of a kit of the compositions and articles described herein to effectively treat a human being in need of treatment for cradle cap.

DETAILED DESCRIPTION OF THE INVENTION AND PREFERRED EMBODIMENTS

Definitions:

As used herein, listed alphabetically below are the components of the shampoo:

"Aloe barbadensis" refers to an aloe healing derivative available from commercial sources. It is usually present in the shampoo composition in between about 0.1 to 0.9 weight percent, preferably between about 0.1 and 0.4 weight percent.

"Annatto extract" refers to a healing extract available from commercial sources. It is usually present in the shampoo composition in between 0.1 to 0.9 weight percent, preferably between about 0.1 and 0.5 weight percent.

"Caramel" refers to conventional caramelized sugar available in the art usually used as a colorizing agent. It is usually present in the shampoo composition in between about 0.01 and 0.09 weight percent, preferably between about 0.04 to 0.09 weight percent.

"Chamomile" or "Camomile" extract refers to the extract of the flower and is commercially available.

"Citric acid" refers to the commercially available acid.

"Cocoamidopropyl hydroxysultane" refers to the commercially available material.

"Decyl glucoside" refers to the commercially available material.

"Disodium EDTA" refers to the disodium salt of ethylenediaminetetraacetic acid. It is available from commercial sources.

"Disodium lauroamphodiacetate" refers to the commercially available material.

"Eucalyptus oil" refers to an oil obtained by boiling eucalyptus (preferably blue gum) leaves in water and condensing the vapor to recover the oil.

"Evening primrose" refers to the extract as commercially available.

"Grapefruit seed extract" refers to the extract as commercially available.

"Methylparaben" refers to a conventional preservative available from commercial sources.

"Panthenol" refers to the commercial material.

"PEG-150 distearate" refers to polyethylene glycol esterified with stearate which is commercially availabale.

"PEG-80 sorbitan laurate" refers to polyethylene glycol which is esterified with sorbitan and laurate and is commercially available.

"Propylparaben" refers to a conventional preservative which is commercially available.

"Purified softened water" refers to conventional softened demineralyzed water.

"Sodium laureth-13 carboxylate" refers to the commercial material.

"Tea Tree oil" or "ti tree oil" refers to the extract as the commercial material.

"Vitamin E acetate" refers to the commercial material.

Also as used herein, the components of the oil are listed below alphabetically:

"Beta-carotene" refers to the commercial material.

"Eucalyptus oil" refers to an oil obtained by boiling eucalyptus (preferably blue gum) leaves in water and condensing the vapor to recover the oil.

"Propylparaben" refers to a conventional preservative which is commercially available.

"Safflower oil" refers to the commercial oil.

"Sweet almond oil" refers to the commercial oil.

"Tea tree oil" or "ti tree oil" refers to the extract as the commercial material.

"Tocopheryl acetate" refers to the commercial material.

"Vitamin A" refers to the commercial material.

"Vitamin D" refers to the commercial material.

All of these components are available from commercial sources. For example, Jason Natural Cosmetics is a manufacturer and formulator of the described composition under contract with the inventors. One of skill in the art is able to obtain all components in effective purity from Jason Natural Cosmetics, 8468 Warner Drive, Culver City, Calif. 90232-2484, telephone (310) 838-7543.

All of the components (ingredients) used in the compositions herein are non-toxic and generally recognized as safe (GRAS) by the U.S. Food and Drug Administration (FDA) at the concentrations described. These components are described in many widely available reference sources, such as the *Merck Index*, published annually by Merck. Inc. of Rahway, N.J., in the *U.S. Pharmacopia*, and in *Chemical Sources USA*.

Cradle cap is the common name for a condition usually in infants caused by overactive sweat and/or oil glands. It is a yellowish, oily, sometimes scaly crust (or scabs) on the scalp. Usually is unsightly, but neither serious nor contagious, and need not be treated. However, if left untreated it has, in the past, become a site of serious infection.

Some of the components listed for the therapeutic oil in Table 2 have been used individually or in some combination for the treatment of cradle cap.

Referring to FIG. 1, is the usual kit of compositions and articles used in the present invention. The improved oil composition is usually provided in a small plastic container 10. Similarly, the improved shampoo composition is usually provided in a small plastic container 11. The caps 10A and 11A may be conventional or have a pour spout. A brush 12 and a sponge 13 are provided. Often they are combined at 12A for ease of handling. The brush 12 is of short flexible plastic bristles to provide a gentle brushing. A single edge or double edge fine tooth comb 14 is included. Written instructions in booklet form 15 to complete the treatment according to the description herein are optionally provided.

While not wanting to be bound by theory or observation, it is believed that the tea tree oil, eucalyptus oil, Vitamin E, camomile extract and/or combinations thereof as the active ingredients in this composition. The other ingredients serve useful functions as carriers, colorants, preservatives and the like.

The components of the shampoo composition and their weight percents are shown in the Summary of the Invention and in Example 1(A).

In more specific compositions, the concentration of the components are as follows:

TABLE 3

More Specific Shampoo Compositions

| COMPONENTS PRESENT IN | WEIGHT PERCENT |
|---|---|
| purified soft water | 70 to 88 |
| PEG (80 sorbitan laurate) | 7 to 8 |
| PEG (150 distearate) | 0.3 to 0.8 |
| disodium - lauroamphodiacetate | 8 to 9 |
| sodium laureth (13 carboxylate) | 3 to 8 |
| cocoamidopropyl hydroxysultane | 3 to 7 |
| decyl glucoside | 4 to 9 |
| tea tree oil | 3 to 8 |
| evening primrose oil | 0.1 to 0.2 |
| aloe barbadensis | 0.1 to 0.5 |
| chamomile extract | 0.1 to 0.4 |
| disodium EDTA | 0.1 to 0.4 |
| citric acid | 0.1 to 0.5 |
| grapefruit seed extract | 0.2 to 0.6 |
| methylparaben | 0.1 to 0.3 |
| propylparaben | 0.005 to .09 |
| annatto extract | 0.01 to 0.06 |
| caramel | 0.04 to 0.09 |
| panthenol | 0.1 to 0.7 |
| vitamin E acetate | 0.1 to 0.5, and |
| eucalyptus oil | 0.1 to 0.5. |

The compositions of the shampoo composition and their weight percents are shown in Example 1(B). In a more specific composition, the concentration of the components are as follows:

TABLE 4

Specific Shampoo Compositions

| COMPONENTS PRESENT IN | WEIGHT PERCENT |
|---|---|
| purified soft water | 70 |
| PBG (80 sorbitan laurate) | 7 |
| PEG (150 distearate) | 0.3 to 0.8 |
| disodium - lauroamphodiacetate | 8 |
| sodium laureth (13 carboxylate) | 3 to 8 |
| cocoamidopropyl hydroxysultane | 3 to 7 |
| decyl glucoside | 4 to 9 |
| tea tree oil | 3 to 8 |
| evening primrose oil | 0.1 to 0.2 |
| aloe barbadensis | 0.1 to 0.5 |
| chamomile extract | 0.1 to 0.4 |
| disodium EDTA | 0.1 to 0.4 |

TABLE 4-continued

Specific Shampoo Compositions

| COMPONENTS PRESENT IN | WEIGHT PERCENT |
|---|---|
| citric acid | 0.1 to 0.5 |
| grapefruit seed extract | 0.2 to 0.6 |
| methylparaben | 0.1 to 0.3 |
| propylparaben | 0.005 to .09 |
| annatto extract | 0.01 to 0.06 |
| caramel | 0.04 to 0.09 |
| panthenol | 0.1 to 0.7 |
| vitamin E acetate | 0.1 to 0.5, and |
| eucalyptus oil | 0.1 to 0.5. |

The compositions of the shampoo composition and their weight percents are shown in Example 1(B). In a specific composition, the concentration of the components are as follows:

TABLE 4A

Specific Shampoo Compositions

| COMPONENTS PRESENT IN | WEIGHT PERCENT |
|---|---|
| purified soft water | 78 |
| PEG (80 sorbitan laurate) | 2 |
| PEG (150 distearate) | 0.3 to 0.8 |
| disodium - lauroamphodiacetate | 4 |
| sodium laureth (13 carboxylate) | 3 to 8 |
| cocoamidopropyl hydroxysultane | 3 to 7 |
| decyl glucoside | 4 to 9 |
| tea tree oil | 3 to 8 |
| evening primrose oil | 0.1 to 0.2 |
| aloe barbadensis | 0.1 to 0.5 |
| chamomile extract | 0.1 to 0.4 |
| disodium EDTA | 0.1 to 0.4 |
| citric acid | 0.1 to 0.5 |
| grapefruit seed extract | 0.2 to 0.6 |
| methylparaben | 0.1 to 0.3 |
| propylparaben | 0.005 to .09 |
| annatto extract | 0.01 to 0.06 |
| caramel | 0.04 to 0.09 |
| panthenol | 0.1 to 0.7 |
| vitamin E acetate | 0.1 to 0.5, and |
| eucalyptus oil | 0.1 to 0.5. |

The components of the oil composition and their weight percents are shown in Example 2(A). In more specific compositions the concentration of these components are as follows:

TABLE 5

More Specific Oil Composition

| COMPONENTS PRESENT IN | WEIGHT PERCENT |
|---|---|
| safflower oil | 60 to 80 |
| sweet almond oil | 5 to 15 |
| tocopheryl acetate | 0.1 to 0.5 |
| beta - carotene | 0.001 to 0.01 |
| tea tree oil | 1 to 6 |
| propylparaben | 0.08 to 0.09 |
| eucalyptus oil | 0.1 to 1 |
| vitamin A | 0.01 to 0.06 |
| vitamin B | 0.01 to 0.1 |

The components of the oil composition and their weight percent are shown in Example 2(B). In specific compositions the concentration of these components are as follows:

TABLE 6

Specific Oil Composition

| COMPONENTS PRESENT IN | WEIGHT PERCENT |
|---|---|
| safflower oil | 80 |
| sweet almond oil | 15 |
| tocopheryl acetate | 0.1 to 0.5 |
| beta - carotene | 0.001 to 0.01 |
| tea tree oil | 1 to 6 |
| propylparaben | 0.08 to 0.09 |
| eucalyptus oil | 0.1 to 1 |
| vitamin A | 0.01 to 0.06 |
| vitamin B | 0.01 to 0.1 |

The components of the oil composition and their weight percent are shown in Example 2(B). In specific compositions the concentration of these components are as follows:

TABLE 6A

Specific Oil Composition

| COMPONENTS PRESENT IN | WEIGHT PERCENT |
|---|---|
| safflower oil | 78 |
| sweet almond oil | 15 |
| tocopheryl acetate | 0.1 to 0.5 |
| beta - carotene | 0.001 to 0.01 |
| tea tree oil | 1 to 6 |
| propylparaben | 0.08 to 0.09 |
| eucalyptus oil | 0.1 to 1 |
| vitamin A | 0.01 to 0.06 |
| vitamin B | 0.01 to 0.1 |

The following examples are meant to be exemplary and illustrative only. They are not to be interpreted to be limiting in any way.

General

The components of the compositions described herein are obtained from standard chemical supply houses listed above and from suppliers such as Aldrich Chemical Company, Milwaukee, Wis. and those listed in *Chemical Sources USA*, published annually by Directories Publishing, Inc. of Boca Raton, Fla.

The more "natural" components or "organic" components are available in high purity from commercial organic materials suppliers. These components are used without further purification.

The components of the oil composition and the range of their weight percents are shown in Example 2(B).

EXAMPLE 1

Preparation of Shampoo Compositions (A) The components of the shampoo composition are added in any order usually starting with the water and adding the components described below in the concentrations listed:

FROM TABLE 5
More Specific Shampoo Composition

| COMPONENTS PRESENT IN | WEIGHT PERCENT |
|---|---|
| purified soft water | 50 to 95 |
| PEG (80 sorbitan laurate) | 1 to 10 |
| PEG (150 distearate) | 0.1 to 1 |
| disodium - lauroamphodiacetate | 1 to 10 |

-continued

FROM TABLE 5
More Specific Shampoo Composition

| COMPONENTS PRESENT IN | WEIGHT PERCENT |
|---|---|
| sodium laureth (13 carboxylate) | 1 to 10 |
| cocoamidopropyl hydroxysultane | 1 to 10 |
| decyl glucoside | 1 to 10 |
| tea tree oil | 1 to 10 |
| evening primrose oil | 0.1 to 0.9 |
| aloe barbadensis | 0.1 to 0.9 |
| chamomile extract | 0.1 to 0.9 |
| disodium EDTA | 0.1 to 0.9 |
| citric acid | 0.1 to 0.9 |
| grapefruit seed extract | 0.1 to 0.9 |
| methylparaben | 0.1 to 0.9 |
| propylparaben | 0.01 to 0.09 |
| annatto extract | 0.01 to 0.09 |
| caramel | 0.01 to 0.09 |
| panthenol | 0.1 to 0.9 |
| vitamin E acetate | 0.1 to 0.9, and |
| eucalyptus oil | 0.1 to 0.9. |

The components are mixed by conventional means for about 0.5 to 2. hr, usually about 1 hr which results in a shampoo.

(B) Example 1(A) is repeated except that the concentration of the shampoo components are those at the concentrations listed below:

FROM TABLE 4
More Specific Shampoo Composition

| COMPONENTS PRESENT IN | WEIGHT PERCENT |
|---|---|
| purified soft water | 70 |
| PEG (80 sorbitan laurate) | 7 |
| PEG (150 distearate) | 0.3 to 0.8 |
| disodium - lauroamphodiacetate | 8 |
| sodium laureth (13 carboxylate) | 3 to 8 |
| cocoamidopropyl hydroxysultane | 3 to 7 |
| decyl glucoside | 4 to 9 |
| tea tree oil | 3 to 8 |
| evening primrose oil | 0.1 to 0.2 |
| aloe barbadensis | 0.1 to 0.5 |
| chamomile extract | 0.1 to 0.4 |
| disodium EDTA | 0.1 to 0.4 |
| citric acid | 0.1 to 0.5 |
| grapefruit seed extract | 0.2 to 0.6 |
| methylparaben | 0.1 to 0.3 |
| propylparaben | 0.005 to .09 |
| annatto extract | 0.01 to 0.06 |
| caramel | 0.04 to 0.09 |
| panthenol | 0.1 to 0.7 |
| vitamin E acetate | 0.1 to 0.5, and |
| eucalyptus oil | 0.1 to 0.5. |

EXAMPLE 2

Preparation of Oil Compositions (A) The components of the oil composition are combined in any order and the components are described below in the concentrations listed:

| FROM TABLE 2 Broad Oil Composition | |
| --- | --- |
| safflower oil | 50 to 90 |
| sweet almond oil | 5 to 25 |
| tocopheryl acetate | 0.1 to 1 |
| beta - carotene | 0.001 to 0.01 |
| tea tree oil | 1 to 10 |
| propylparaben | 0.01 to 0.09 |
| eucalyptus oil | 0.1 to 1 |
| vitamin A | 0.01 to 0.1 |
| vitamin B | 0.01 to 0.1 |

The composition is mixed by conventional means for about 0.5 to 2 hr, usually about 1 hr, which results in a therapeutic oil.

(B) Example 2(A) is repeated except that the concentration of the oil components are those at the concentrations listed in Table 5.

EXAMPLE 3

Treatment of Cradle Cap (A) An infant exhibiting a cradle cap condition of the scalp with many scales is placed on an appropriate surface. The oil composition of Example 2(A) about ⅛ to 1 teaspoon is gently rubbed onto the scalp scales for about 2 min. After 30 sec. to 2 hr of contact with the oil, the scalp of the infant is treated using a brush to gently loosen the scales on the scalp and to carefully remove the scales. The scalp is then washed with about 1 teaspoon of the shampoo of Example 1(A) dissolved in water (about 1 pint to 10 pints). Repeating this treatment procedure once a day usually cures the cradle cap within 1 to 5 days.

(B) The method of Example 3(A) is repeated except that 1 teaspoon of oil and 1 teaspoon of shampoo is used.

(C) The method of Example 3(A) is repeated except that ½ teaspoon of the oil of Example 2(B) is used and 1/2 teaspoon of shampoo of Example 1(B) is used.

(D) The method of Example 3(C) is repeated except that one tablespoon of the oil of Example 2(B) and 1 tablespoon of the shampoo of Example 1(B) is used.

EXAMPLE 4

Treatment of Cradle Cap

Example 3(A) is repeated except that the oil composition of Example 2(A) about 0.5 teaspoon is applied for 3 to 4 min. The scale in the scalp area and oil are removed by using the shampoo of Example 1(A) (about 1 teaspoon) in 5 pints of water and the scalp is rinsed with warm water. By repeating this treatment once a day for 2 to 3 days, is sufficient to eliminate the cradle cap.

EXAMPLE 5

Treatment of Cradle Cap

Example 3(A) is repeated except that about ¼ to ½ teaspoon of the oil composition of Example 2(A) is applied to the scalp of an infant having cradle cap. After about 5 minutes, the oil is removed by washing with water and about 1 teaspoon of the shampoo of Table 1. Three to four days of this treatment once a day eliminates the cradle cap.

EXAMPLE 6

Treatment of Cradle Cap

Example 3(A) is repeated except that the oil (about 1 teaspoon) is sponged (brushed) onto the scalp. After 5 min. the oil is sponged, and the area is brushed to remove scales. The area is then shampooed to remove scales.

EXAMPLE 7

Treatment of Cradle Cap

Example 3(D) is repeated using 1–2 teaspoons of the oil. After 15 min. a small fine tooth comb is used to brush the area and lift the scales. The area is then shampooed. After once a day treatment, for 3–5 days, the cradle cap is gone.

EXAMPLE 8

Treatment of Cradle Cap

Example 3(A) was repeated and the cradle cap was gone in 5 days. When cured, the cradle cap does not return.

EXAMPLE 9

Treatment of Cradle Cap

A two year old girl had cradle cap for over two years. The method of Example 3(D) was repeated, the cradle cap was gone and did not return.

While only a few embodiments of the invention have been shown and described herein, it will become apparent to those skilled in the art that various modifications and changes can be made in the improved shampoo composition and the improved oil composition and the method of treatment of cradle cap without departing from the spirit and scope of the present invention. All such modifications and changes coming within the scope of the appended claims are intended to be carried out thereby.

We claim:

1. A therapeutic shampoo composition for a human infant to reduce or eliminate the condition of cradle cap, which shampoo composition comprises:

the following components present in between about the range weight present indicated:

| COMPONENTS PRESENT IN | WEIGHT PERCENT (WT. %) |
| --- | --- |
| purified soft water | 50 to 95 |
| PEG (80 sorbitan laurate) | 1 to 10 |
| PEG (150 distearate) | 0.1 to 1 |
| disodium - lauroamphodiacetate | 1 to 10 |
| sodium laureth (13 carboxylate) | 1 to 10 |
| cocoamidopropyl hydroxysultane | 1 to 10 |
| decyl glucoside | 1 to 10 |
| tea tree oil | 1 to 10 |
| evening primrose oil | 0.1 to 0.9 |
| aloe barbadensis | 0.1 to 0.9 |
| chamomile extract | 0.1 to 0.9 |
| disodium EDTA | 0.1 to 0.9 |
| citric acid | 0.1 to 0.9 |
| grapefruit seed extract | 0.1 to 0.9 |
| methylparaben | 0.1 to 0.9 |
| propylparaben | 0.01 to 0.09 |
| annatto extract | 0.01 to 0.09 |
| caramel | 0.01 to 0.09 |
| panthenol | 0.1 to 0.9 |
| vitamin E acetate | 0.1 to 0.9, and |
| eucalyptus oil | 0.1 to 0.9. |

2. The therapeutic shampoo composition of claim 1 wherein purified soft water is present in between about 60 to 90 weight percent.

3. The therapeutic shampoo composition of claim 1 wherein the tea tree oil is present in about 3 to 9 weight percent.

4. The therapeutic shampoo composition of claim 1 wherein the eucalyptus oil is present in between about 0.3 and 0.5 weight percent.

5. The therapeutic shampoo composition of claim 1 wherein decyl glucoside is present in between about 2 and 9 weight percent.

6. A therapeutic oil composition for a human infant to reduce or eliminate the disease condition of cradle cap, which oil composition comprises:

the following compounds which are present in between about the weight percent range indicated:

| COMPONENTS PRESENT IN | WEIGHT PERCENT (WT. %) |
|---|---|
| safflower oil | 50 to 90 |
| sweet almond oil | 5 to 25 |
| tocopheryl acetate | 0.1 to 1 |
| beta - carotene | 0.001 to 0.01 |
| tea tree oil | 1 to 10 |
| propylparaben | 0.01 to 0.09 |
| eucalyptus oil | 0.1 to 1 |
| vitamin A | 0.01 to 0.1, and |
| vitamin B | 0.01 to 0.1. |

7. The therapeutical oil composition of claim 6 wherein the safflower oil is present in between about 1 to 6 weight percent.

8. The therapeutic oil composition of claim 6 wherein the sweet almond oil is present in between about 4 and 20 weight percent.

9. A therapeutic shampoo composition for a human infant to reduce or eliminate the condition of cradle cap, which shampoo composition comprises:

the following components present in between about the range weight present indicated:

| COMPONENTS PRESENT IN | WEIGHT PERCENT (WT. %) |
|---|---|
| purified soft water | 70 to 88 |
| PEG (80 sorbitan laurate) | 7 to 8 |
| PEG (150 distearate) | 0.3 to 0.8 |
| disodium - lauroamphodiacetate | 8 to 9 |
| sodium laureth (13 carboxylate) | 3 to 8 |
| cocoamidopropropyl hydroxysultane | 3 to 7 |
| decyl glucoside | 4 to 9 |
| tea tree oil | 3 to 8 |
| evening primrose oil | 0.1 to 0.2 |
| aloe barbadensis | 0.1 to 0.5 |
| chamomile extract | 0.1 to 0.4 |
| disodium EDTA | 0.1 to 0.4 |
| citric acid | 0.1 to 0.5 |
| grapefruit seed extract | 0.2 to 0.6 |
| methylparaben | 0.1 to 0.3 |
| propylparaben | 0.005 to .09 |
| annatto extract | 0.01 to 0.06 |
| caramel | 0.04 to 0.09 |
| panthenol | 0.1 to 0.7 |
| vitamin E acetate | 0.1 to 0.5, and |
| eucalyptus oil | 0.1 to 0.5. |

10. The therapeutic shampoo composition of claim 9 wherein purified soft water is present in between about 75 to 85 weight percent.

11. The therapeutic shampoo composition of claim 10 wherein the PEG (80 sorbitan laurate) is present in about 2 to 9 weight percent.

12. The therapeutic shampoo composition of claim 10 wherein the tea tree oil is present in between about 4 and 7 weight percent.

13. The therapeutic shampoo composition of claim 9 wherein decyl glucoside is present in between about 2 and 9 weight percent.

14. A therapeutic oil composition for a human infant to reduce or eliminate the disease condition of cradle cap, which oil composition comprises:

the following compounds which are present in between about the weight percent range indicated:

| COMPONENTS PRESENT IN | WEIGHT PERCENT (WT. %) |
|---|---|
| safflower oil | 60 to 80 |
| sweet almond oil | 5 to 15 |
| tocopheryl acetate | 0.1 to 0.5 |
| beta - carotene | 0.001 to 0.01 |
| tea tree oil | 1 to 6 |
| propylparaben | 0.08 to 0.09 |
| eucalyptus oil | 0.1 to 1 |
| vitamin A | 0.01 to 0.06, and |
| vitamin B | 0.01 to 0.1. |

15. The therapeutical oil composition of claim 14 wherein the safflower oil is present in between about 65 to 75 weight percent.

16. The therapeutic oil composition of claim 15 wherein the sweet almond oil is present in between about 4 and 14 weight percent.

17. A method to treat cradle cap in a human being, which method comprises:

(a) contacting the scalp or related area of a human being in need of treatment with an effective amount of a therapeutic oil composition itself comprising:

| COMPONENTS PRESENT IN | WEIGHT PERCENT (WT. %) |
|---|---|
| safflower oil | 50 to 90 |
| sweet almond oil | 5 to 25 |
| tocopheryl acetate | 0.1 to 1 |
| beta - carotene | 0.001 to 0.01 |
| tea tree oil | 1 to 10 |
| propylparaben | 0.01 to 0.09 |
| eucalyptus oil | 0.1 to 1 |
| vitamin A | 0.01 to 0.1, and |
| vitamin B | 0.01 to 0.1. | rubbing the therapeutic oil composition in thoroughly into the area exhibiting cradle cap and allowing the oil to remain on the skin surface for between about 1 and 60 min followed by using a brush to gently loosen the scales on the scalp and removing the scales;

(b) contacting the scalp or related area of the human being with an effective amount of a shampoo composition itself comprising:

| COMPONENTS PRESENT IN | WEIGHT PERCENT (WT. %) |
|---|---|
| purified soft water | 50 to 95 |
| PEG (80 sorbitan laurate) | 1 to 10 |
| PEG (150 distearate) | 0.1 to 1 |
| disodium - lauroamphodiacetate | 1 to 10 |
| sodium laureth (13 carboxylate) | 1 to 10 |
| cocoamidopropropyl hydroxysultane | 1 to 10 |
| decyl glucoside | 1 to 10 |

-continued

| COMPONENTS PRESENT IN | WEIGHT PERCENT (WT. %) |
|---|---|
| tea tree oil | 1 to 10 |
| evening primrose oil | 0.1 to 0.9 |
| aloe barbadensis | 0.1 to 0.9 |
| chamomile extract | 0.1 to 0.9 |
| disodium EDTA | 0.1 to 0.9 |
| citric acid | 0.1 to 0.9 |
| grapefruit seed extract | 0.1 to 0.9 |
| methylparaben | 0.1 to 0.9 |
| propylparaben | 0.01 to 0.09 |
| annatto extract | 0.01 to 0.09 |
| caramel | 0.01 to 0.09 |
| panthenol | 0.1 to 0.9 |
| vitamin E acetate | 0.1 to 0.9, and |
| eucalyptus oil | 0.1 to 0.9. | and water to remove the therapeutic oil composition and loose cradle cap particles;

(c) repeating step (a) and step (b) as needed for a 1 to 5 day period or until the cradle cap condition disappears.

18. The method of claim 17 to treat cradle cap in a human being, which method comprises:

(a) contacting the scalp or related area of a human being in need of treatment with a therapeutic oil composition itself comprising:

| COMPONENTS PRESENT IN | WEIGHT PERCENT (WT. %) |
|---|---|
| safflower oil | 60 to 80 |
| sweet almond oil | 5 to 15 |
| tocopheryl acetate | 0.1 to 1 |
| beta - carotene | 0.001 to 0.01 |
| tea tree oil | 1 to 10 |
| propylparaben | 0.01 to 0.09 |
| eucalyptus oil | 0.1 to 1 |
| vitamin A | 0.01 to 0.1, and |
| vitamin B | 0.01 to 0.1. | rubbing the therapeutic oil composition thoroughly into the area exhibiting cradle cap and allowing the therapeutic oil to remain on the skin surface for between about 1 and 60 min followed by using a brush to gently loosen the scales on the scalp and removing the scales (b) contacting the scalp or related area of the human being with an effective amount of the shampoo composition itself comprising:

| COMPONENTS PRESENT IN | WEIGHT PERCENT (WT. %) |
|---|---|
| purified soft water | 70 to 88 |
| PEG (80 sorbitan laurate) | 7 to 8 |
| PEG (150 distearate) | 0.3 to 0.8 |
| disodium - lauroamphodiacetate | 8 to 9 |
| sodium laureth (13 carboxylate) | 3 to 8 |
| cocoamidopropyl hydroxysultane | 3 to 7 |
| decyl glucoside | 4 to 9 |
| tea tree oil | 3 to 8 |
| evening primrose oil | 0.1 to 0.2 |
| aloe barbadensis | 0.1 to 0.5 |
| chamomile extract | 0.1 to 0.4 |
| disodium EDTA | 0.1 to 0.4 |
| citric acid | 0.1 to 0.5 |
| grapefruit seed extract | 0.2 to 0.6 |
| methylparaben | 0.1 to 0.3 |
| propylparaben | 0.005 to .09 |
| annatto extract | 0.01 to 0.06 |
| caramel | 0.04 to 0.09 |
| panthenol | 0.1 to 0.7 |
| vitamin E acetate | 0.1 to 0.5, and |
| eucalyptus oil | 0.1 to 0.5. | and water to remove the oil and loose cradle cap particles;

(c) repeating step (a) and step (b) as needed for a 1 to 5 day period or until the cradle cap condition disappears.

19. The method of claim 18 wherein the tea tree oil in the shampoo is present in about 8 weight percent.

20. A kit comprising oil, a shampoo composition, a brush, a sponge, a fine toothed comb, and a set of instructions to treat cradle cap according to the method described in claim 17.

* * * * *